US007264599B1

(12) United States Patent
Milligan

(10) Patent No.: US 7,264,599 B1
(45) Date of Patent: Sep. 4, 2007

(54) MASSAGING BATHING SHOE

(76) Inventor: ShellyAnn S Milligan, 105-20 172nd St., Jamaica, NY (US) 11433-1752

( * ) Notice: Subject to any disclaimer, the term of this patent is extended or adjusted under 35 U.S.C. 154(b) by 301 days.

(21) Appl. No.: 10/978,075

(22) Filed: Oct. 28, 2004

Related U.S. Application Data

(60) Provisional application No. 60/516,414, filed on Nov. 3, 2003.

(51) Int. Cl.
*A61F 5/14* (2006.01)
*A61H 7/00* (2006.01)

(52) U.S. Cl. .......................... 601/28; 601/30; 601/136; 36/8.1; 36/141

(58) Field of Classification Search .................. 601/28, 601/30, 31, 104, 136, 138; 36/3 B, 30 R, 36/11.5, 8.1, 141; 4/541.5, 622
See application file for complete search history.

(56) References Cited

U.S. PATENT DOCUMENTS

| | | | | |
|---|---|---|---|---|
| 1,257,086 | A * | 2/1918 | Marcellus | 36/2.6 |
| 3,888,242 | A * | 6/1975 | Harris et al. | 601/152 |
| 4,215,491 | A * | 8/1980 | Giannetti | 36/8.1 |
| 5,113,850 | A * | 5/1992 | Larremore et al. | 601/46 |
| 5,758,370 | A * | 6/1998 | Schwartz | 4/622 |

* cited by examiner

*Primary Examiner*—Quang D. Thanh
(74) *Attorney, Agent, or Firm*—Michael I. Kroll

(57) ABSTRACT

A waterproof bathing slipper having a plurality of nodules for massaging and stimulating specific parts of the soles and sides of the users feet. The present invention includes static and electrically operated pulsating nodules disposed in such a manner as to stimulate specific regions of the foot as applied by the principles of reflexology.

11 Claims, 13 Drawing Sheets

MASSAGING BATHING SHOE

RELATED APPLICATIONS

This application is subject to U.S. provisional application Ser. No. 60/516,414, filed 3 Nov. 2003.

Please incorporate by reference all information in said provisional application into this instant application.

BACKGROUND OF THE INVENTION

1. Field of the Invention

The present invention relates generally to footwear and, more specifically, to a waterproof bathing slipper having a plurality of nodules for massaging and stimulating specific parts of the soles and sides of the users feet. The present invention includes static and electrically operated pulsating nodules disposed in such a manner as to stimulate specific regions of the foot as applied by the principles of reflexology.

The bathing slipper of the present invention may be adapted to different types of footwear such as flip-flops and sandals to name a few.

2. Description of the Prior Art

There are other footwear devices designed for massaging the user's feet. While these devices may be suitable for the purposes for which they where designed, they would not be as suitable for the purposes of the present invention as heretofore described.

It is thus desirable to provide a massaging bathing shoe that uses batteries to actuate pulsating nodules that will stimulate the soles and sides of the user's feet. Static nodules are also provided and will stimulate the user's feet when standing or moving.

It is further desirable to provide a massaging bathing shoe that provides a means for removing water therefrom without the user having to remove the shoe to do so.

SUMMARY OF THE PRESENT INVENTION

A primary object of the present invention is to provide a massaging bathing shoe having a plurality of electrically operated pulsating nodules to stimulate specific sections of the user's feet as determined by reflexology charts.

Another object of the present invention is to provide a massaging bathing shoe that further includes a plurality of static nodules that massage the user's feet with the movement and the pressure applied by the user.

Yet another object of the present invention is to provide a massaging bathing shoe that has a low voltage power source and isolated wiring and circuitry to provide safe, maintenance free electricity to the pulsating nodules.

Still yet another object of the present invention is to provide a massaging bathing shoe with an external power switch to enable the user to actuate and deactivate the pulsating nodules as needed while wearing the shoes.

Another object of the present invention is to provide a massaging bathing shoe that may be adapted for use with other styles of footwear.

Yet another object of the present invention is to provide a massaging bathing shoe that is simple and easy to use.

Still yet another object of the present invention is to provide a massaging bathing shoe that is inexpensive to manufacture and operate.

Additional objects of the present invention will appear as the description proceeds.

The foregoing and other objects and advantages will appear from the description to follow. In the description reference is made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

Figure 1:
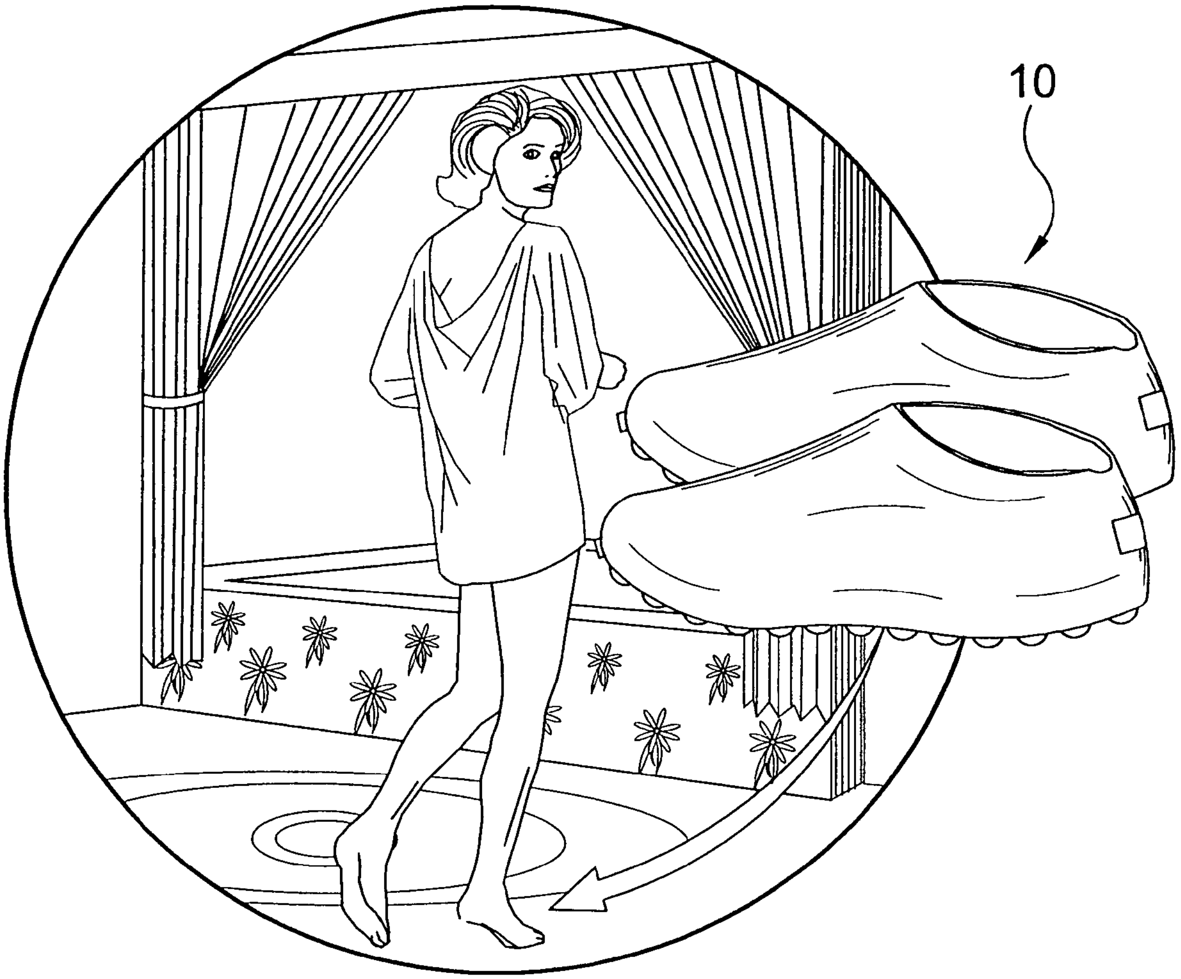
FIG. 1 is an illustrative view of the present invention in use.

Turning now descriptively to the drawings, in which similar reference characters denote similar elements throughout the several views, the figures illustrate the Massaging Bathing Shoe of the present invention. With regard to the reference numerals used, the following numbering is used throughout the various drawing figures.

10 Massaging Bathing Shoe of the present invention
12 insole
14 outsole
16 static cleansing and massage nodules
18 pulsating nodules
19 pulsating nodule groups
20 battery
21 on/off switch
22 electrical connection
24 drain valve
25 drain conduit
26 one-way check valve
28 reservoir
30 reservoir drain conduit

32 insert plug
34 nodule grips
36 hand pump
38 thermoelectric drain valve

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments, practitioners skilled in the art will recognize numerous other embodiments as well. For definition of the complete scope of the invention, the reader is directed to appended claims.

FIG. 1 is an illustrative view of the present invention in use. The present invention 10 is a bathing shoe or foot wear worn in a bath, shower, poolside, your backyard or beach that helps prevent contact with various germs on a walking surface.

Figure 2:
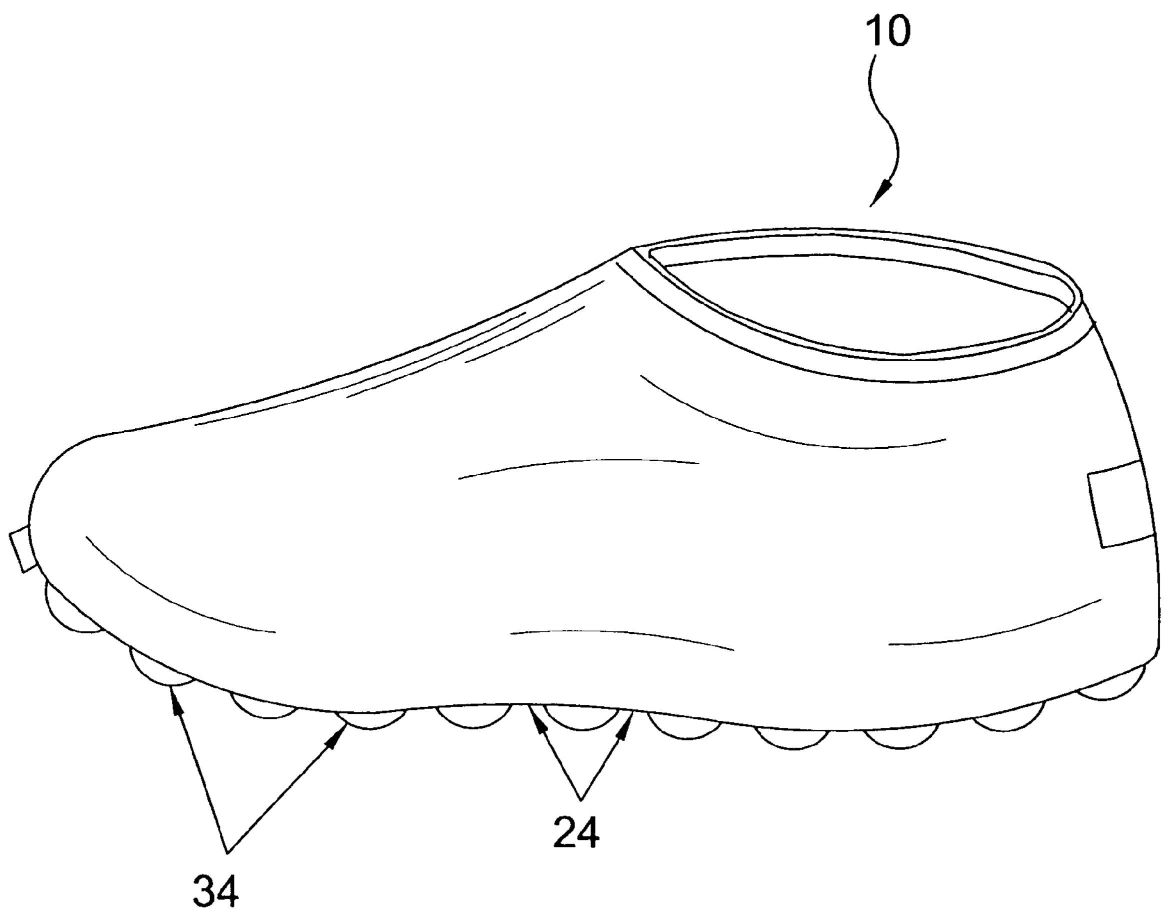
FIG. 2 is a perspective view of the present invention.

FIG. 2 is a perspective view of the present invention 10. Shown is the present invention 10, a bathing shoe or footwear worn in a bath, shower, poolside or at the beach that helps prevent contact with various fungi or germs on a walking surface. Further comprising one-way drain valves 24 and massage and cleansing nodules. The bottom of said footwear incorporates gripping nodules 34 designed to be skid resistant to protect the wearer while walking or standing on slippery surfaces.

Figure 3:
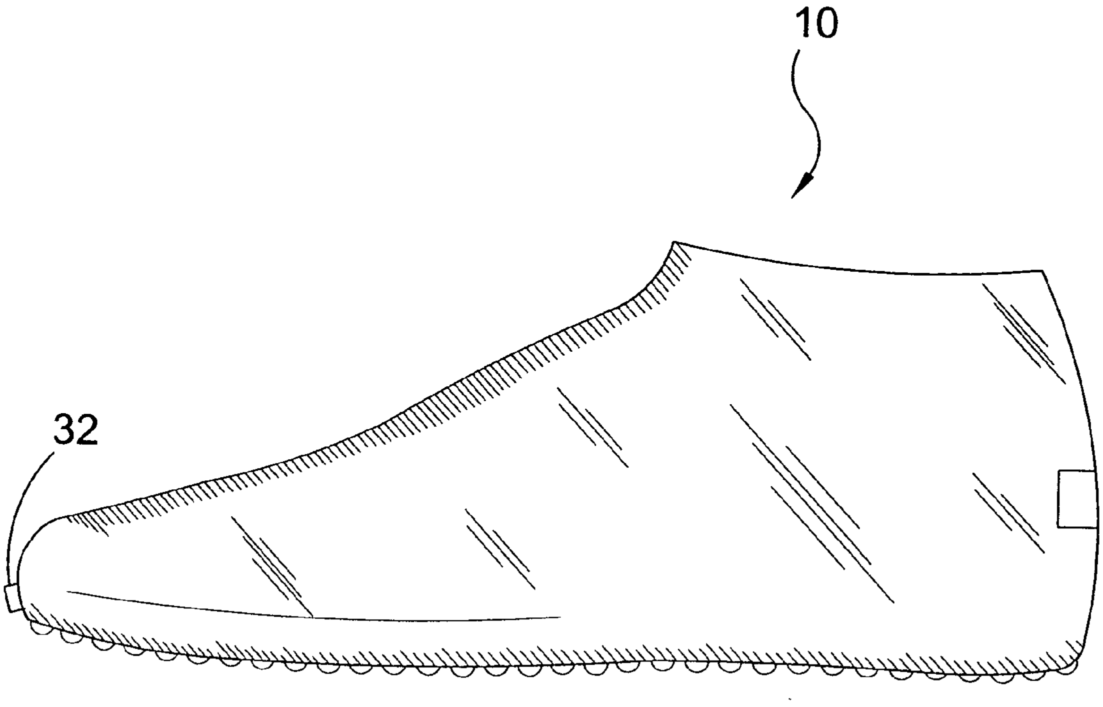
FIG. 3 is a side view of the present invention.

FIG. 3 is a side view of the present invention 10. Shown is the present invention 10, a bathing shoe or foot wear worn in a bath, shower, pool side or beach that helps prevent contact with infection from various germs on a walking surface. A removable insert plug 32 is included to allow for removal of fluid from the shoe without the user having to remove it from the foot.

Figure 4:
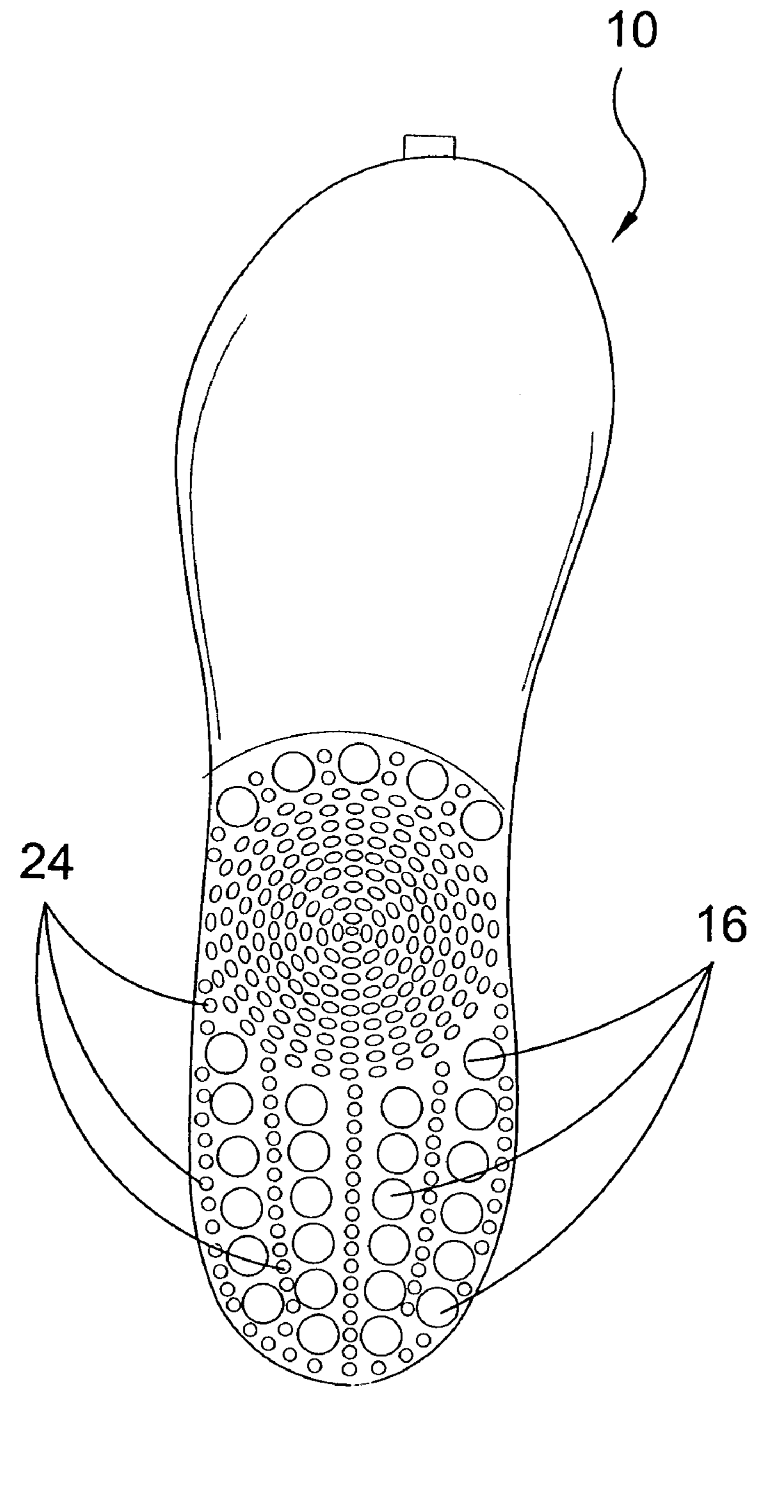
FIG. 4 is a top view of the present invention.

FIG. 4 is a top view of the present invention 10. Shown is the present invention 10, a bathing shoe or foot wear worn in a bath, shower, pool side or beach that helps prevent contact with various fungi or germs on a walking surface. Further comprising one-way drain valves 24 disposed between massage and cleansing nodules 16.

Figure 5:
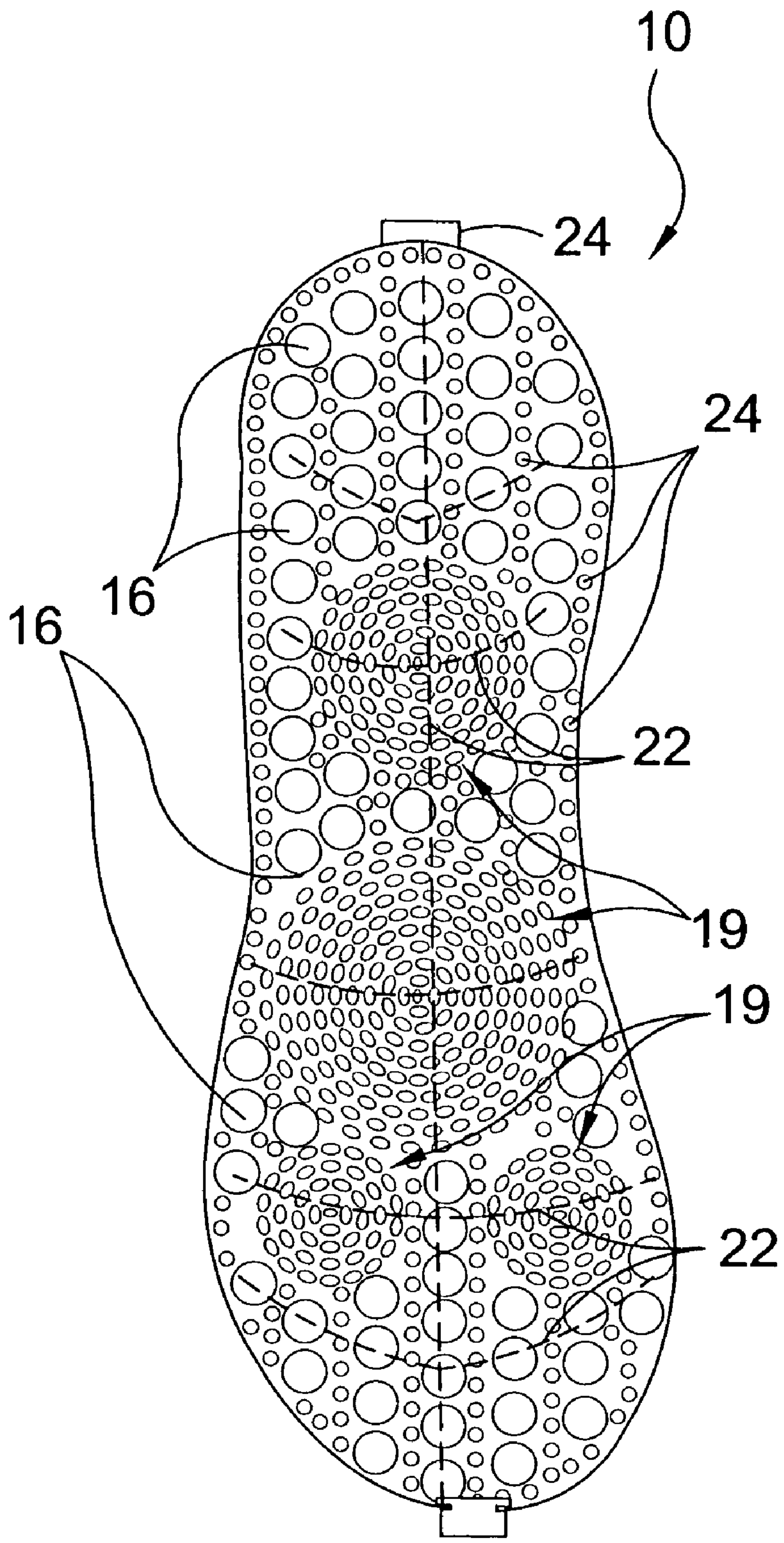
FIG. 5 is a top view of the sole of the present invention.

FIG. 5 is a top view of the sole of the present invention. Shown is the insole of the present invention comprising three vital components: a plurality of non-special static nodules 16, a plurality of electrically operated specialized pulsating nodules 18 arranged in groups 19 that provide a pulsating up and down massage motion upon command and a plurality of drain valves 24. The arrangement shown is for illustrative purposes and may be reconfigured accordingly without deviating from the object and intent of the present invention. The arrangement of the preferred embodiment of the present invention has the specialized nodules 18 grouped together and positioned to provide a penetrating massage in specific areas as defined by reflexology. The shoes of the present invention 10 may be manufactured with the special nodule groups 19 in different sizes and locations to stimulate various organs and body areas as required by the needs of the user. Low voltage electricity from a battery 20 is used to provide safety under all condition and the electrical connections 22 are isolated to further enhance safety and to assure the integrity of the electrical circuit during usage. Any suitable wiring configuration may be used and one possible wiring scheme is demonstrated in the illustration. However, the specific method of supplying electricity to the pulsating nodules 18 requiring power may be altered, modified and changed without affecting objectives and the gist of the present invention.

Figure 6:
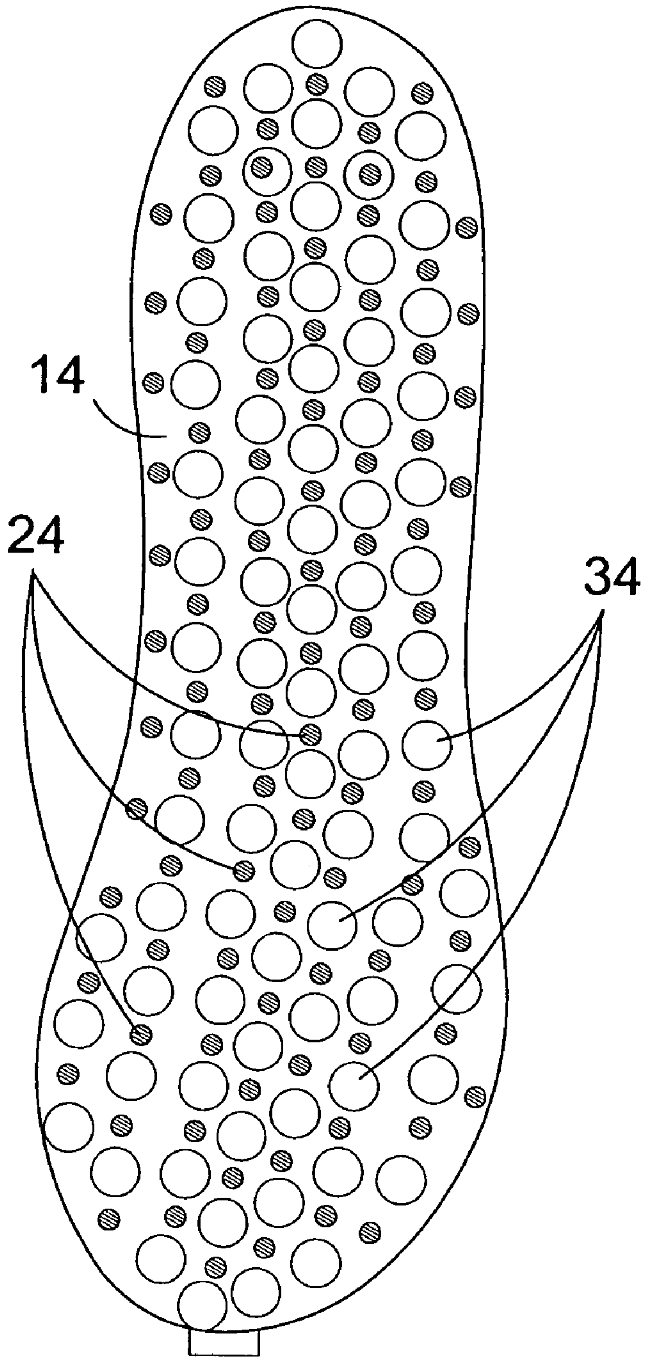
FIG. 6 is a bottom view of the sole of the present invention.

FIG. 6 is a bottom view of the outsole 14 of the present invention 10. Shown is the outsole 14 of the present invention 10. The bottom of said footwear incorporates gripping nodules 34 designed to be skid resistant to protect the wearer while walking or standing on slippery surfaces.

Figure 7:
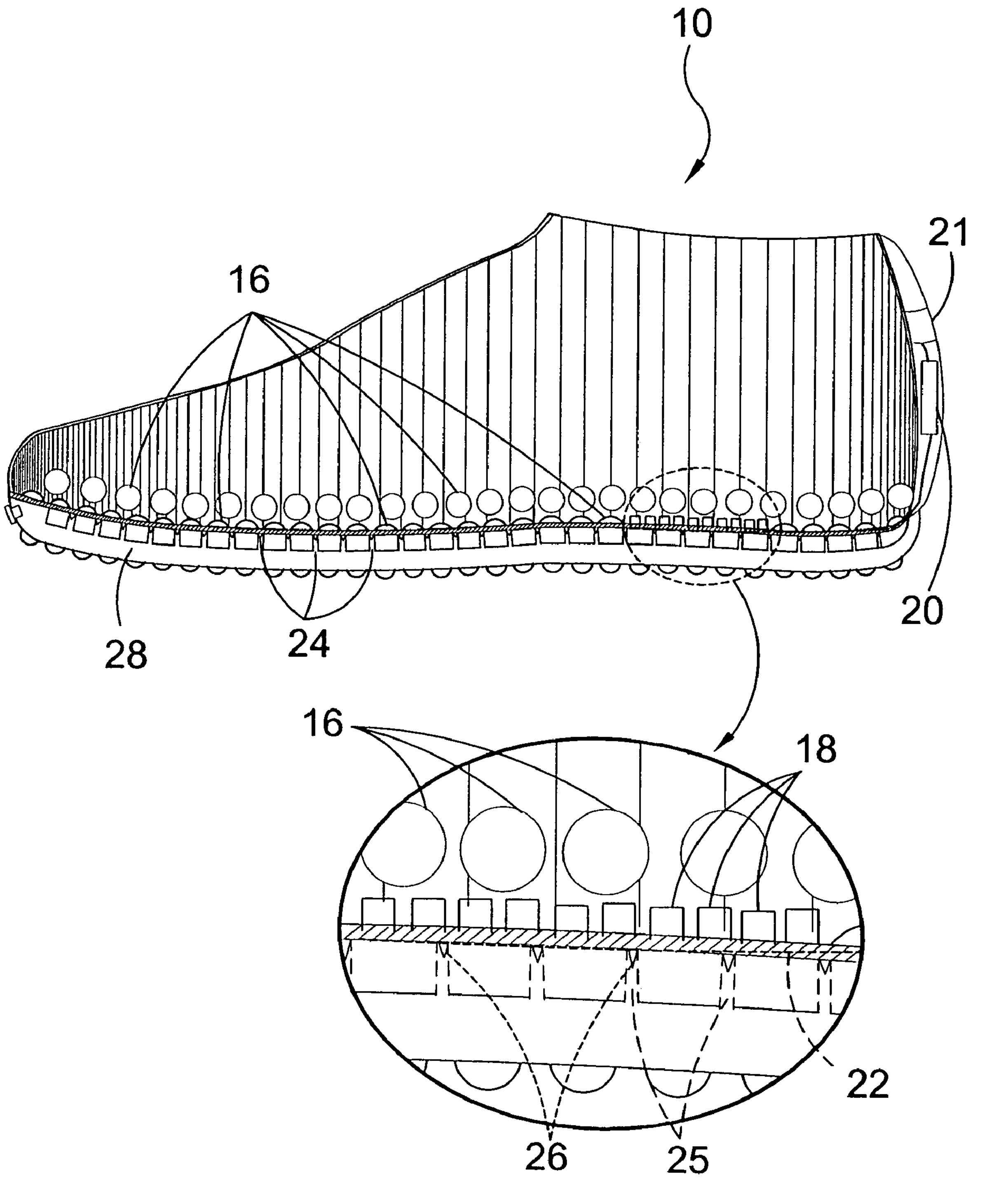
FIG. 7 is a sectional view of the present invention.

FIG. 7 is a sectional view of the present invention 10. Shown is a sectional view of the present invention 10 showing the bottom and side cleaning modules 16 inside the shoe and the electrically operated specialized nodules 18. A battery 20 supplies the power to the specialized nodules 18 when the power switch 21 is turned on thereby initiating the up and down motion of the nodules 18 on the insole 12 and sides of the shoe. Shown is one possible wiring configuration to supply power to the nodules 18 on the sides and the sole although any other suitable configuration may be adapted without altering the concept of the present invention.

Figure 8:
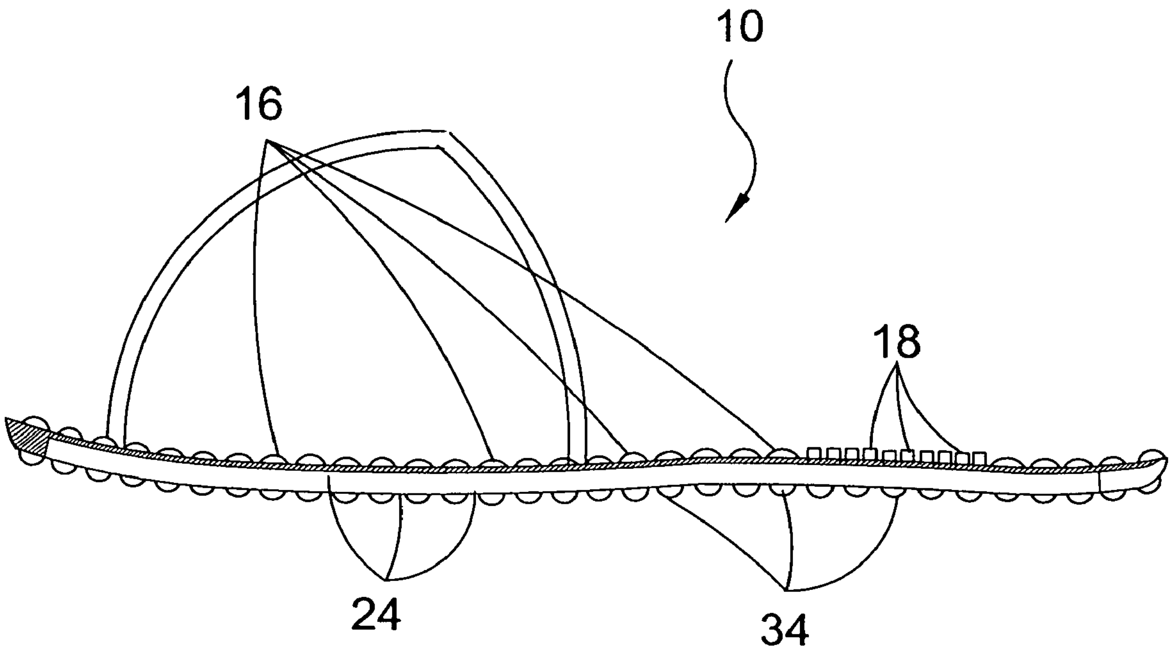
FIG. 8 is a sectional view of the present invention.

FIG. 8 is a sectional view of the present invention 10 adapted to a flip-flop. Shown is a sectional view of the present invention 10 showing the pulsating nodules 18 and the static cleaning and massage nodules 16 on the top and a plurality of nodule grips 34 on the bottom.

Figure 9:
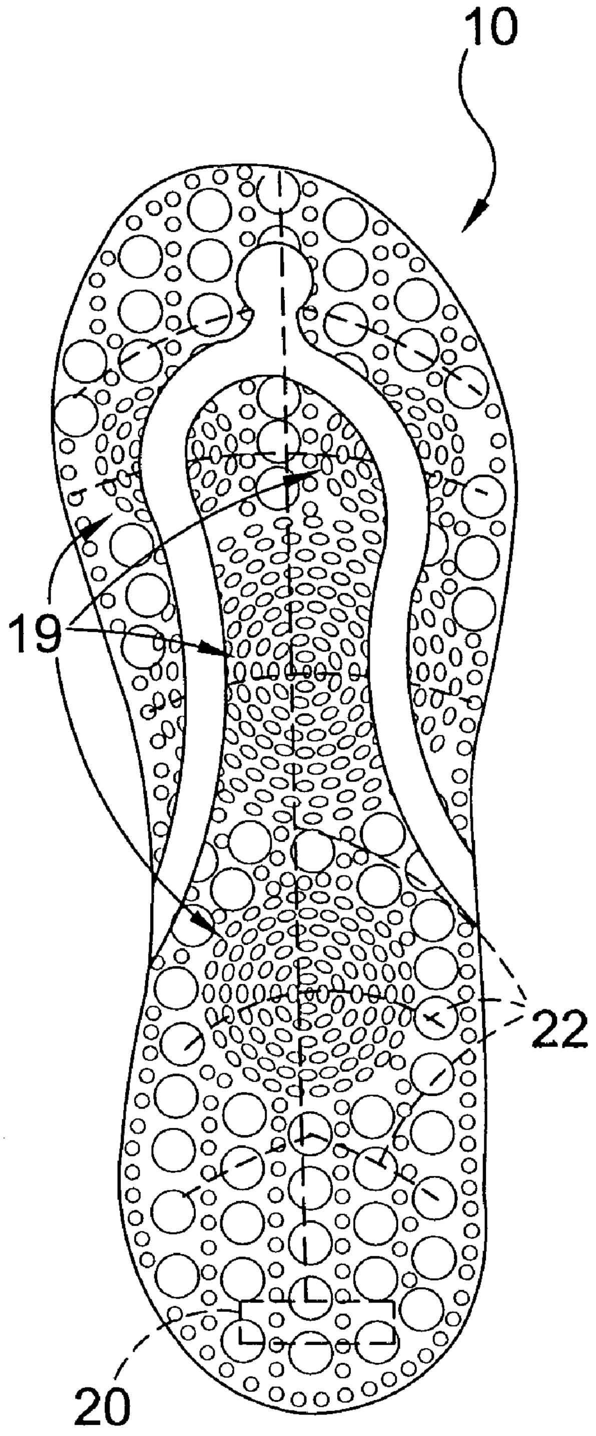
FIG. 9 is a top view of another variation of the present invention.

FIG. 9 is a top view of the flip-flop variation of the present invention 10. Shown is one possible wiring configuration for the electrical connections 22 to supply power from the imbedded battery 20 to the pulsating nodule groups 19 to provide for the up and down movement thereof for the vibrating/penetration action against the user's feet.

Figure 10:
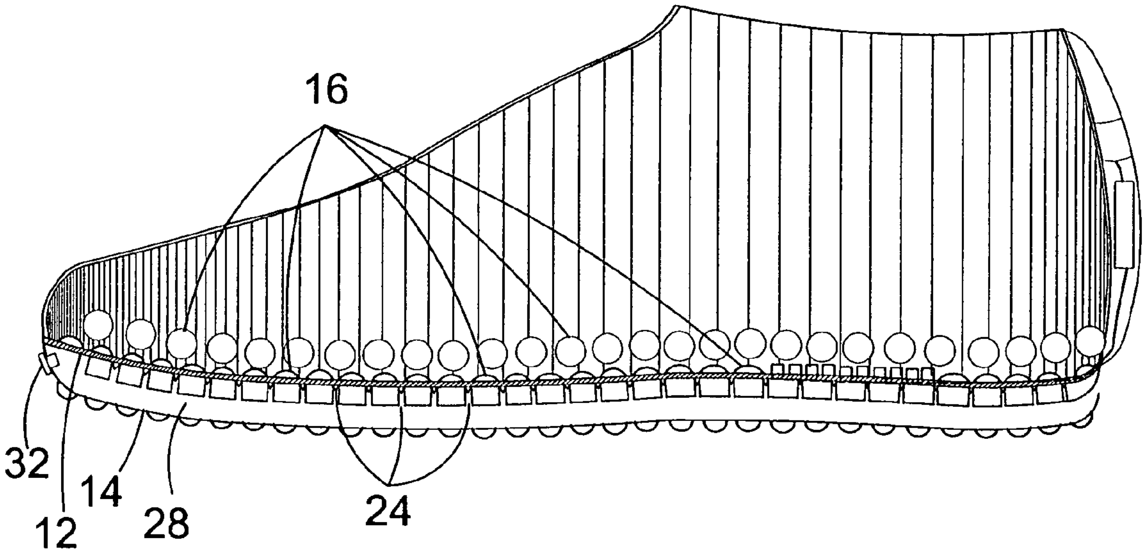
FIG. 10 is a sectional view of option A of the drain assembly of the present invention.

FIG. 10 is a sectional view of option A of the drain assembly of the present invention. Shown is option "A" of the drain assembly wherein a reservoir 28 is disposed between the insole 12 of the shoe and the outsole 14 to receive and retain excess water prior to draining. Water in the shoe passes through the one-way drain valves 24 into the reservoir. A threaded plug 32 is included to provide a point of egress to drain the reservoir 28 and the shoe without the user having to remove the shoe to do so. The electrical components have been omitted for reasons of clarity and because they have heretofore been duly addressed. The alternate options of the present invention 10 do not change the objectives thereof as the present invention 10 comprises a plurality of electrically operated pulsating massage nodules 18 and passive nodules 16 strategically positioned to take advantage of the principles of reflexology, a means for retaining fluid therein and a means for removing the fluid therefrom without removing the shoe. The alternate options of the present invention 10 seek to demonstrate some of the possible means for removing the fluid therefrom but said means is in no way limited to the methods shown in the illustrations.

Figure 11:
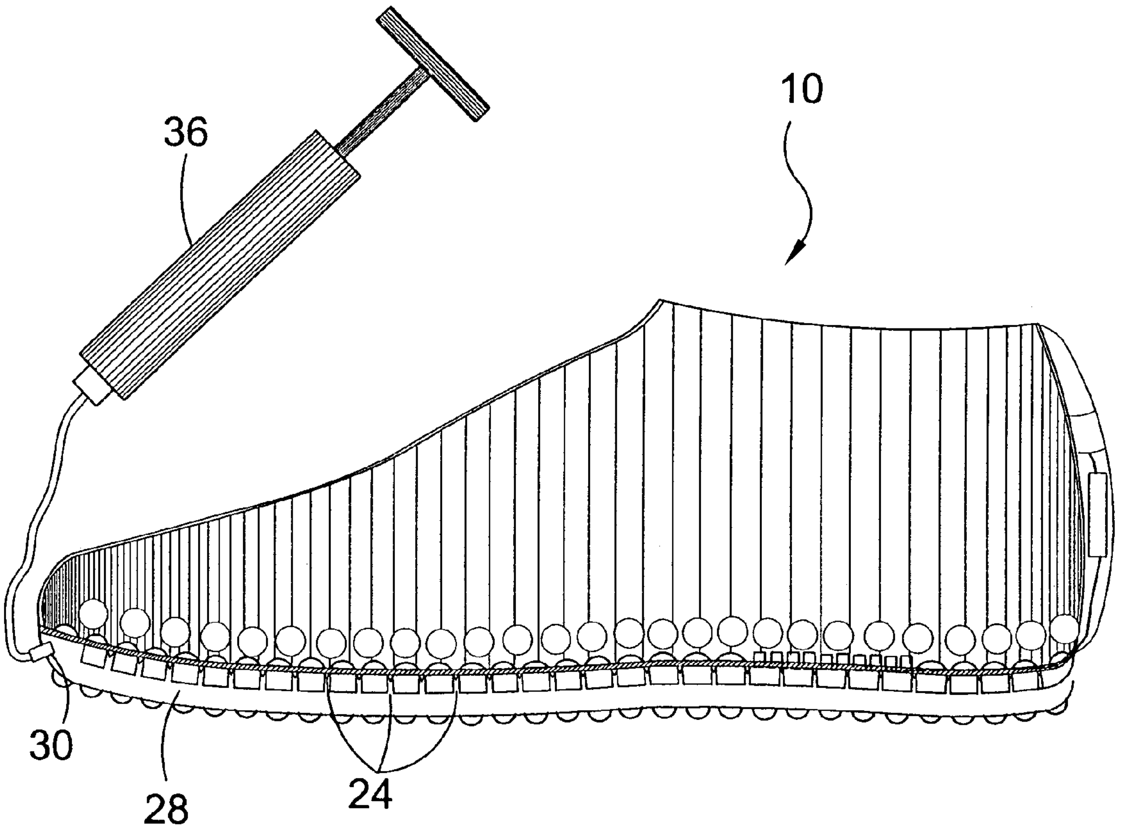
FIG. 11 is a sectional view of option B of the drain assembly of the present invention.

FIG. 11 is a sectional view of option B of the drain assembly of the present invention 10. Shown is option "B" of the drain assembly having the reservoir 28 as depicted in option "A" and further including a hand pump 36 that screws into the threaded recess of the reservoir drain conduit 30 for the threaded drain plug. Withdrawing the handle extracts all the water from the shoe.

Figure 12:
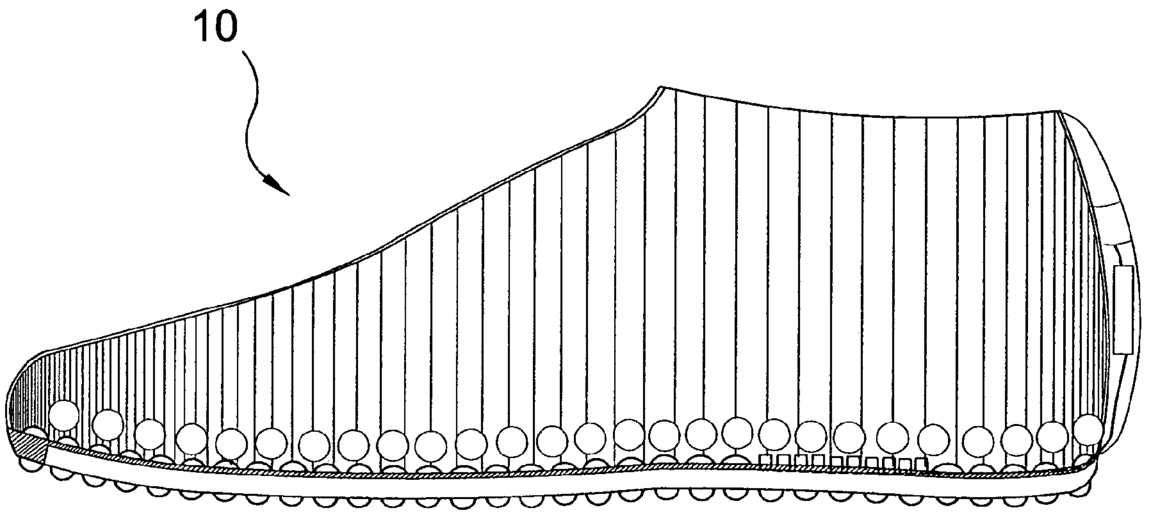
FIG. 12 is a sectional view of option C of the present invention.

FIG. 12 is a sectional view of option C of the present invention 10. Shown is a sectional view of the present invention 10 having all components as shown in FIGS. 1–11 with the drain valve elements eliminated. The user removes the water from the shoe simply by removing the shoe and pouring the water out.

Figure 13:
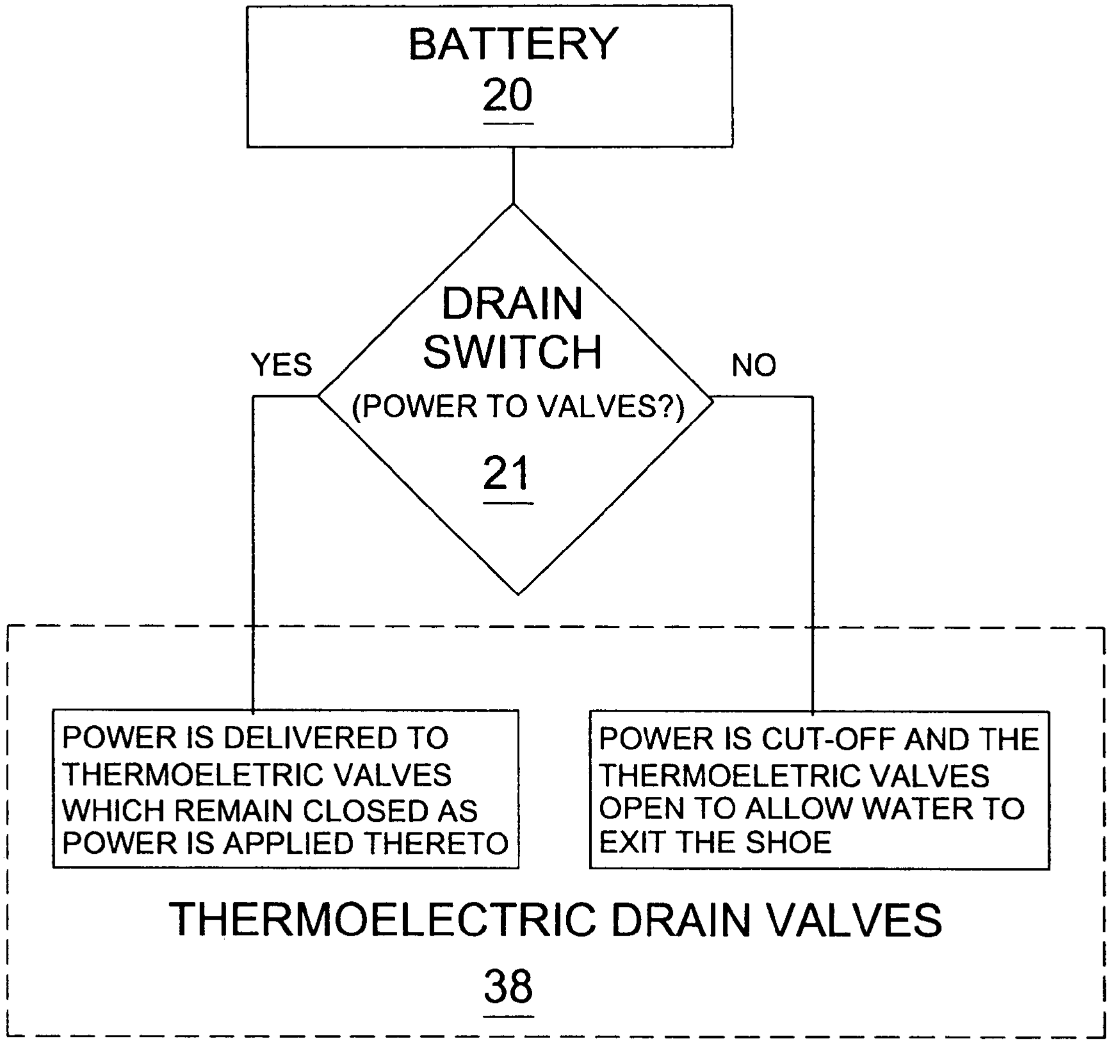
FIG. 13 is a flow chart of option D of the drain assembly of the present invention.

FIG. 13 is a flow chart of option D of the drain assembly of the present invention 10. Shown is a flow chart depicting the drain valves 38 of the present invention 10 having thermoelectric properties wherein the thermoelectric valves 38 remain closed as long as an electrical charge is applied thereto. A drain switch 21 is provided for the user to open when the shoe needs to be drained and the thermoelectric valves 38 respond to the absence of an electrical charge by opening and letting water pass therethrough to the exterior of the shoe. One-way check valves remain in place within the thermoelectric valves 38 to ensure that no exterior water enters the shoes through the valves.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A massaging bathing shoe comprising:

a) a shoe fabricated of an impermeable material capable of retaining a fluid therein while being worn by the user;

b) a plurality of massage nodules disposed within the interior of said shoe; and c) means for draining the fluid from said shoe while being worn by the user without having to remove said shoe; and said draining means comprises:

d) a reservoir disposed between an insole and an outsole of said shoe;

e) a plurality of drain conduits communicating between the interior of said shoe and said reservoir;

f) one-way check valves disposed within said drain conduits to allow for passage of fluid from the interior of said shoe to said reservoir while restricting the flow of fluid from said reservoir to the interior of said shoe;

g) a reservoir drainage conduit communicating between said reservoir and the exterior of said shoe; and h) a removable, insertable drain plug for insertion into said reservoir drainage conduit to prevent the egress of fluid from said reservoir until the user so desires.

2. A massaging bathing shoe as recited in claim 1, wherein said massage nodules are static and massage the bottom and sides of the user's feet through the motion and pressure applied during the movement of the user.

3. A massaging bathing shoe as recited in claim 2, wherein said massage nodules further include a plurality of electrically operated pulsating nodules arranged to stimulate specific areas.

4. A massaging bathing shoe as recited in claim 3, wherein said pulsating nodules are powered by at least one battery.

5. A massaging bathing shoe as recited in claim 4, further including a power switch disposed on an exterior portion of said shoe wherein said pulsating nodules are selectively activated and deactivated by the user as needed.

6. A massaging bathing shoe as recited in claim 1, wherein said reservoir drainage conduit and said drain plug further include mating threads to provide a secure means of maintaining said drain plug within said reservoir drainage conduit.

7. A massaging bathing shoe as recited in claim 6, wherein said draining means further includes a pump having a suction line with a threaded end that is threaded into said reservoir drainage conduit for removing fluid from said reservoir and said interior of said shoe.

8. A massaging bathing shoe as recited in claim 1, wherein said draining means is a plurality of thermoelectric drain valves extending through said insole wherein electrical power is applied thereto to keep the valves closed until an on/off switch is turned to disconnect power to the valve thereby opening to allow fluid to pass from the interior of the shoe through said insole.

9. A massaging bathing shoe comprising:

a) a shoe fabricated of an impermeable material capable of retaining a fluid therein while being worn by the user;

b) a plurality of massage nodules disposed within the interior of said shoe; and c) means for draining the fluid from said shoe while being worn by the user without having to remove said shoe;

d) wherein said massage nodules are static and massage the bottom and sides of the user's feet through the motion and pressure applied during the movement of the user, e) wherein said massage nodules further include a plurality of electrically operated pulsating nodules arranged to stimulate specific areas.

10. A massaging bathing shoe as recited in claim 9, wherein said pulsating nodules are powered by at least one battery.

11. A massaging bathing shoe as recited in claim 10, further including a power switch disposed on an exterior portion of said shoe wherein said pulsating nodules are selectively activated and deactivated by the user as needed.

* * * * *